US009101143B2

(12) United States Patent
Markus et al.

(10) Patent No.: US 9,101,143 B2
(45) **Date of Patent: *Aug. 11, 2015**

(54) FORMULATIONS CONTAINING MICROENCAPSULATED ESSENTIAL OILS

(75) Inventors: Arie Markus, Beer Sheva (IL); David Schuster, Bradenton, FL (US); Charles Linder, Rehovot (IL); Pnina Strongin, Beer-Sheva (IL)

(73) Assignee: BOTANOCAP LTD. (IL)

( * ) Notice: Subject to any disclaimer, the term of this patent is extended or adjusted under 35 U.S.C. 154(b) by 481 days.

This patent is subject to a terminal disclaimer.

(21) Appl. No.: 11/795,866

(22) PCT Filed: Jul. 4, 2005

(86) PCT No.: PCT/IL2005/000705

§ 371 (c)(1), (2), (4) Date: Oct. 2, 2007

(87) PCT Pub. No.: WO2006/077568

PCT Pub. Date: Jul. 27, 2006

(65) Prior Publication Data

US 2008/0166415 A1 Jul. 10, 2008

(51) Int. Cl.
*A01N 25/12* (2006.01)
*A01N 65/00* (2009.01)

(52) U.S. Cl.
CPC .................................... *A01N 65/00* (2013.01)

(58) Field of Classification Search
None
See application file for complete search history.

(56) References Cited

U.S. PATENT DOCUMENTS

| | | | | |
|---|---|---|---|---|
| 2,463,324 | A * | 3/1949 | Simanton | 514/68 |
| 4,668,666 | A * | 5/1987 | Allan et al. | 514/63 |
| 5,549,903 | A * | 8/1996 | Marcus | 424/408 |
| 5,576,009 | A | 11/1996 | Nastke et al. | |
| 5,925,464 | A | 7/1999 | Mulqueen et al. | |
| 5,928,634 | A * | 7/1999 | Uick et al. | 424/84 |
| 8,753,676 | B2 * | 6/2014 | Kritzman et al. | 424/451 |

FOREIGN PATENT DOCUMENTS

| | | | | |
|---|---|---|---|---|
| EP | 0 252 897 A2 | | 1/1998 | |
| WO | 94/13139 | | 6/1994 | |
| WO | 2004/098767 A1 | | 11/2004 | |
| WO | WO 2004/098767 | * | 11/2004 | B01J 13/16 |

OTHER PUBLICATIONS

XP-002369787: Zhang, z. "Antiviral medical preparation of Curuma zedoaria oil and its preparation", Chemical Abstract Service, Columbus, Ohio,pp. 1-2.

* cited by examiner

*Primary Examiner* — Brian Gulledge
(74) *Attorney, Agent, or Firm* — Whitmyer IP Group LLC

(57) ABSTRACT

The present invention provides for a novel "green" agricultural formulation comprising at least one encapsulated volatile essential oil and a non-volatile vehicle in which said at least one encapsulated volatile essential oil is carried.

23 Claims, No Drawings

FORMULATIONS CONTAINING MICROENCAPSULATED ESSENTIAL OILS

CROSS-REFERENCE TO RELATED APPLICATIONS

This application is a National Stage of International patent application PCT/IL2005/000705 filed on Jul. 4, 2005 which designated the United States and claimed priority from U.S. patent application Ser. No. 11/040,102 filed on Jan. 24, 2005.

FIELD OF THE INVENTION

This invention relates to formulations containing microencapsulated essential oils.

BACKGROUND OF THE INVENTION

Prior to the development of the modern chemical and pharmaceutical industries essential oils were used in many areas of daily life as antiseptic and disinfectant materials in pharmaceutical and cosmetic applications such as antimicrobial and larvicidal agents. Essential oil based formulations with a broad spectrum of antimicrobial activity have been shown to be relatively nontoxic to mammals. They have been replaced with more potent synthetic chemicals and antibiotics, which are cheaper and highly effective and can be used in lower concentrations. With time, however, the toxicity and environmental effects of these synthetic chemicals have been revealed, and there is now an effort to replace them with the same essential oil agents that they had originally replaced.

The use of such essential oil based formulations in agriculture has also been reported. PCT Publication No. WO 04/098767 (Application No. PCT/IL2004/000394), to the inventors of the present application, disclose microcapsules of essential oils which may be used as disinfectant products for the consumer market as hard-surface cleaners, laundry detergents and softeners, as pesticides, insect repellents, and as antiviral or antifungal agents. When the microcapsules are applied to given substrates, the essential oil contained therein is released at a constant rate over a period of time. The efficacy of such microcapsules depends solely on parameters relating to the microcapsules themselves, i.e., size, thickness of the encapsulating membrane, ability to sustain release of the essential oil contained therein, etc., and not on the aqueous medium which carries them to the target environment and which dries immediately thereafter.

SUMMARY OF THE INVENTION

It has now been found, in accordance with the present application, that the efficacy of encapsulated volatile essential oils as pesticides, repellents, ovicides, larvicides and antiviral agents may increase if they are suspended or dispersed in a non-volatile vehicle, which may contain such agents as high boiling or high melting essential oils and lipids. More specifically it has been determined that the efficacy of these encapsulated volatile oils increases, if, upon application to the substrate or target environment, they remain, for example, upon evaporation of an aqueous medium, in contact with a non-volatile agent, which is capable of enhancing the exerted effect. It has also been surprisingly found that the effect of the non-volatile vehicle may be additive or synergistic.

Thus, the present invention provides an agricultural formulation comprising at least one encapsulated volatile essential oil and a non-volatile vehicle, in which said at least one encapsulated volatile essential oil is carried. The non-volatile vehicle may be a solid or a liquid vehicle.

The expression "encapsulated essential oil" or "encapsulation" or any lingual variation thereof refers herein to a granule of any shape and size, which is capable of holding therein one or more essential oils. One example of such encapsulation is microencapsulation. Although the agricultural formulation of the present application, without affecting its benefits, may make use of any encapsulated essential oil granules known in the art, the preferred granule form is of a microcapsule. The preferred microcapsule is one having from 30 to 98%, or more preferably from 60-95%, of its weight a volatile essential oil and which is prepared by interfacial polymerization of isocyanates. Such polymerization affords a microencapsulating shell of polyurethanes, polyureas or combinations thereof, as disclosed for example in WO 04/098767. Such a microcapsule typically has an average size of between 0.1 and 100 microns. Other suitable microcapsules may be prepared by such methods as disclosed for example in WO 94/13139, EP0252897, U.S. Pat. No. 5,576,009 and U.S. Pat. No. 5,925,464.

Thus, the present invention more specifically provides an agricultural formulation comprising at least one microcapsule containing volatile essential oil, and a non-volatile vehicle.

The term "non-volatile vehicle" as used herein refers generally to an organic agent that remains with the microcapsule on the target environment after application and which exerts an additive or synergistic effect. Such a vehicle may be a liquid or a solid (pure or mixture) having a high boiling or melting point and which rate of evaporation from the surface of the target environment, after application thereto, is smaller as compared to the encapsulated essential oil. Such vehicles or carriers may for example be non-volatile essential oils, non-volatile botanical oils, non-volatile or solid terpenes, and lipids.

The vehicle is never water alone. However, in various embodiments it may be necessary that water be the major component of the formulation. In such exemplary cases when the microcapsules are made in aqueous solutions, or when water is added to allow better fluidity and sprayabillity or when the formulation is packaged or stored in water, the non-volatile vehicle may be added to the water solution which acts as a medium and has no beneficial effect on the repelling, insecticidal, pesticidal, larvicidal or ovicidal characteristics of the formulation. As it will be described hereinbelow, after application of the formulation, the water evaporates leaving behind the microcapsule suspended in the non-volatile vehicle. In other embodiments, water may not be necessary.

When said vehicle is a liquid essential oil or a lipid, the term refers to those having boiling points higher then 300° C. Such high boiling point essential oils may for example be pyrethrins. An example of a lipid is sesame oil or cottonseed oil.

The term "solid vehicle" refers to a solid agent, pure or mixture, in which the microcapsules are admixed and which may be dissolved in, suspended in or dispersed evenly in a liquid medium, e.g. water, prior to application onto the target. Solid vehicles may for example be in the form of powders. The term "liquid vehicle" refers to a pure liquid, to a homogeneous liquid mixture of agents (each of which before mixing may be a solid, a liquid, or a gas) or to a heterogeneous mixture of such agents, e.g. suspension, in which said encapsulated essential oils e.g., microcapsules may be suspended. The suspension of the microcapsules in the liquid vehicle or in the solution prepared by dissolving or dispersing a solid vehicle in an appropriate medium, as for example water, should be such that the consistency, distribution, physical state, or concentration of the volatile essential oil within the microcapsule is not affected. Such vehicle additionally is one in which said microcapsules do not dissolve, deteriorate, decompose, leach out or undergo any other physical or chemical transformation. The term "suspended" or any other lingual variation thereof refers to a state of dispersion of the microcapsules in the vehicle or a dispersion of the microcapsules and vehicle in a non-miscible liquid; by way of a non-limiting example the dispersion is of cottonseed oil and microcapsules in water. The term may alternatively refer to a state of colloid, depending on the size of the microcapsules.

In one embodiment, said non-volatile vehicle is at least one non-volatile essential oil, at least one non-volatile botanical oil or any combination thereof. Such combinations may for example be, without being limited thereto: (a) a combination of two or more different non-volatile essential oils; (b) a combination of two or more different non-volatile essential oils with at least one botanical oil; (c) a combination of one non-volatile essential oil with one non-volatile botanical oil; (d) a combination of two different non-volatile botanical oils, and the like. Similar variations may also be made with any one specific sub-group, e.g. lipids and with any one specific representative thereof, as for example different triglycerides.

The terms "volatile", "moderately volatile" and "non-volatile" refer to the degree of evaporative ability of the chemical agent under ambient temperature and pressure. Typically, the lower the agent's boiling point is the more volatile the agent is said to be. In reference to essential oils, the volatile, low boiling point oils are those defined as having boiling points lower than about 250° C. The moderately volatile oils are those defined as having boiling points of between 250° C. and 300° C. The non-volatile or less volatile oils are those defined as having boiling points higher then 300° C.

"Botanical oils" are natural complex mixtures of oils made by plants. "Essential oils" are those that in general give to the plants their characteristic odors, flavors, or other such properties. Botanical oils are found in various parts of the plant body (in the seeds, flowers, bark, or leaves) and are also concentrated in certain special cells or groups of cells (glands). In general, they are complex mixtures that may be obtained from the plant in various ways, depending upon the nature of the part in which they are found. Such methods may for example be by compression, by distillation with steam, by dissolving the oils out (extraction) or absorbing them, and by pressure and maceration. The term also refers to oil mixtures prepared by enriching naturally obtained botanical oil with one or more specific component such as monoterpenes, diterpenes, triterpenes, tetraterpenes, sesquiterpenes, and other polyterpenes as well as organic alcohols, aldehydes ketones, acids and esters.

While the terms "essential oils" and "botanical oils" are used in different literary sources interchangeably, within the scope of the present invention the latter refers to a larger group of compounds that also includes lipids.

"Lipids" as referred to herein include the fatty, acids, the glycerol-derived lipids (including the fats and oils and the phospholipids), the sphingosine-derived lipids (including the ceramides, cerebrosides, gangliosides, and sphingomyelins), the steroids and their derivatives, the terpenes and their derivatives, certain aromatic compounds, and long-chain alcohols and waxes. The term also refers to lipoproteins (lipids conjugated with proteins or carbohydrates), to lipopolysaccharides and to vitamins such as fat-soluble vitamins.

In a preferred embodiment, the botanical oils are selected from sesame oil, pyrethrum, glycerol-derived lipids or glycerol fatty acid derivatives and the said at least one encapsulated essential oil is selected from cinnamon, cedar, clove, geranium, lemongrass, mint, sesame, thyme oil, turmeric oil, wintergreen oil, rosemary, anise oil, cardamom oil, chamomile oil, coriander oil, cumin oil, dill oil, mint oil, parsley oil, basil, camphor, citronella, eucalyptus, fennel, ginger, grapefruit, lemon, mandarin, orange, pine needle, pepper oil, rose oil, sweet orange oil, tangerine, tea tree, tea seed, caraway, garlic, peppermint oil, onion, and spearmint oil. Preferably, essential oils are volatile and may be chosen without limitation from citronella, geranium, tea tree, lavender, clove pine and eucalyptus.

In another embodiment of the present invention, the formulations of the present invention may also comprise adjuvants, adhesives, antioxidants, water-resistant agents, surfactants, steric barrier polymers which prevent microcapsule aggregation and gel-breaking agents, as part of the vehicle or within the microcapsule.

Adjuvants may be used for example to improve shelf life, sprayabillity, and adsorption to the substrate. Such adjuvants may be chosen from both natural and synthetic polymers such as polyvinyl alcohol, polyvinylpyrrolidone, polyethylene oxides, ethylene or maleic anhydride copolymers, methyl vinyl ether-maleic anhydride copolymer, water-soluble cellulose, water soluble polyamides or polyesters, copolymers or homopolymers of acrylic acids, water-soluble starches and modified starches, natural gums such as alginates, dextrins and proteins such as gelatins and caseins.

In another embodiment, the formulation may also comprise pesticides such as insect growth regulators (IGR), herbicides, insecticides, acaracides, fungicides, nematicides, ectoparasiticides, and/or herbicides either within the microcapsule or as part of the vehicle. Preferably, said formulation may contain pesticides which are soluble in either said at least one encapsulated essential oil or in the non-volatile vehicle. Such pesticides may for example be carbamates, ureas, triazines, triazoles, uracils, organophosphates, morpholines, dinitroanilines, acylalaninies, pyrethroids, and organochlorines. Specific examples are carbofuran, azinphos-methyl, sulfentrazone, carfentrazone-ethyl, cypermethrin, cyromazine, beta-cyfluthrin, endosulfan, phosmet, chlorobromuron, chloroxuron, chlorotoluron, fluometuron, metobromuron, thiazafluron, teflubenzuron, hexaflumuron, diflubenzuron, flufenoxuron, lufenuron, chlorfluazuron, novaluron, dimethachlor, metolachlor, pretilachlor, 2-chloro-n-(1-methyl-2-methoxyethyl)-acet-2,6-xylidide, alachlor, butachlor, propachlor, dimethenamid, bifenox, 4-(4-pentyn-1-yloxy) diphenylether, acifluorfen, oxyfluorfen, fluoroglycofen-ethyl, fomesafen, cis,trans-(+)-2-ethyl-5-(4-phenoxyphenoxymethyl)-1,3-dioxolane, fluazifop-butyl, haloxyfop-methyl, haloxyfop-(2-ethoxyethyl), fluorotopic, fenoxapropethyl, quizalofop-ethyl, propaquizafop, diclofop-methyl, butralin, ethalfluralin, fluchloralin, isopropalin, pendimethalin, profluralin, trifluralin, imidocloprid, aclalanines furalaxyl, metalaxyl, benzoylprop ethyl, flamprop methyl, difenoconazole, etaconazol, propiconazole, 1,2-(2,4-dichlorophenyl)-pent-1-yl-1h-1,2,4-triazole, triadimefon, dioxacarb, furathiocarb, aldicarb, benomyl, endosulfan, 2-sec-butylphenylmethylcarbamate, etiofencarb, fenoxycarb, isoprocarb, propoxur, carbetamid, butylate, di-allat, eptc, molinate, thiobencarb, tri-allate, vemolate, piperophos, anilofos, butamifos, azamethiphos, chlorfenvinphos, dichlorvos, diazinon, methidathion, azinphos ethyl, azinphos methyl, chlorpyrifos, chlorthiofos, crotoxyphos, cyanophos, demeton, dialifos, dimethoate, disulfoton, etrimfos, famphur, flusulfothion, fluthion, fonofos, fornothion, heptenophos, isofenphos, isoxathion, malathion, mephospholan, mevinphos, naled, oxydemeton methyl, oxydeprofos, parathion, phoxim, pyrimiphos methyl, profenofos, propaphos, propetamphos, prothiophos, quinalphos, sulprofos, phemephos, terbufos, triazophos, trichloronate, fenamipos, isazophos, s-benzyl-o,o-diisopropylphosphorothioate, edinphos, and pyrazophos.

The physical state of the formulation, namely as a solid or liquid, depends on whether the non-volatile vehicle is a liquid or a solid or whether the non-volatile vehicle and microcapsules are suspended or dispersed in an immiscible liquid such as water. Regardless of its physical state, the formulation may be put to use by further forming it into a desirable preparation form, such as an emulsifiable concentrate, a wettable powder, a granular wettable powder, a flowable preparation, a suspension, a granule, a dust, a fumigant and the like. The nature of the preparation form may be decided based on such parameters as the target environment, the method of application, the conditions under which the application is performed, the relative concentration of the microcapsules in the non-volatile vehicle, etc.

Although the concentration of the microcapsules in the non-volatile vehicle may be controlled, the concentration of the encapsulated essential oil may vary depending on storage, climate conditions, preparation form, method of application, place of application, objective pests to be controlled, objective crop plant, and the like. The concentration of volatile essential oils within a formulation may vary between 0.01 to 90%, or preferably from 0.1 to 25%. With respect to applications to the target environment, e.g. a crop field, the volatile essential oils may be appropriately selected from a range of 0.1% and preferably 0.25% in terms of weight of volatile essential oil, per field.

Without wishing to be bound by theory, when, for example, an aqueous based formulation is applied to the target environment, the water therein dries on the surface, leaving a layer of the non-volatile vehicle in which the encapsulated volatile essential oils are embedded. The initial effect on the treated environment is exerted by the nonvolatile vehicle; slowly thereafter, be it through spontaneous release or by any other initiated release, the microcapsules begin releasing their content, thereby both affecting either an additive or synergistic effect on the environment.

The formulations of the present invention may be adaptable to the four profiles of microcapsule release, namely (1) a rapid release profile; (2) a sustained or a delayed release profile; (3) a so-called "knock-down" biological effect profile under which the microcapsule releases its content as one portion or over a relatively short time; and (4) a residuality profile in which the so-called "knock-down" is followed by a sustained release profile.

The formulation of the present invention may be used for various agricultural, horticultural and agronomic purposes dependent on the specific essential oils used. The term "agricultural formulation" also refers to horticultural and agronomic formulations. Without wishing to be bound by theory and modes of operation, the formulations may act as repellents by driving the pests off without ensuing their death; as insecticides (or pesticides) by killing a part of or a whole population of insects or other pests; and as ovicides by killing a part or a whole population of insect eggs. The term "pest" refers also to insects, nematodes, and to any other injurious animal to humans, animals and plant varieties. Examples of pests are those belonging to the heteroptera of hemiptera, homoptera, coleoptera, leopidoptera, thysanoptera, hymenoptera, isoptera, orthoptera, acarina, dolylamida, gstopoda and tylenchida.

Examples for pests belonging to heteroptera are plataspid bug (*Megacopta punctatissimum*), whitespotted bug (*Eysarcoris parvus*), southern green stinkbug (*Nezara viridula*), brownwinged green bug (*Plautia stali*), rice bug (*Leptocorisa chinensis*), bean bug (*Riptortus clavatus*), rice leaf bug (*Togo hemipterus*), pear lace bug (*Stephanitis nashi*), azelea lace bug (*Stephanitis pyrioides*), pale green plant bug (*Apolygus spinolai*), narrow squash bug (*Cletus puctiger*), sorghum plant bug (*Stenotus rubrovittalus*), whitespotted larger spined bug (*Eysarcoris lewisi*) and rice leaf bug (*Trigonotylus coelestialium*).

Examples of pests belonging to coleoptera are cupreous chafer (*Anomala cuprea*), powderpost beetle (*Lyctus bruneus*), confused flour beetle (*Tribolium confusum*), twenty-eight-spotted ladybird (*Epilachna vigintioctopunctata*), Japanese beetle (*Popillia japonica*), whitespotted longicorn beetle (*Anoplophora malasiaca*), Japanese pine sawyer (*Monochamus alteratus*), azuki bean weevil (*Callosobruchus chinensis*), rootworm (*Diabrotica* spp.), boll weevil (*Anthonomus grandis grandis*), pepper weevil (*Anthonomus eugenii*), cucurbit leaf beetle (*Aulacophora femoralis*), Mexican beetle (*Epilachna varivestis*), Colorado leaf beetle (*Leptinotarsa decemlineata*), rice water weevil (*Lissorhoptrus oryzophylus*), rice leaf beetle (*Oulema oryzae*), and hunting billbug (*Sphenophrus venatus vestitus*).

Examples of pests belonging to homoptera are leafhopper (*Arboridia apicalis*), tea green leafhopper (*Empoasca onukii*), green rice leafhopper (*Nephotettix cincticeps*), green rice leafhopper (*Nephotettix virescens*), small brown planthopper (*Laodelphax striatellus*), brown rice planthopper (*Nilaparvata lugens*), whitebacked rice planthopper (*Sogatella furcifera*), citrus psylla (*Diaphorina citri*), citrus spiny whitefly (*Aleurocanthus spiniferus*), silverleaf whitefly (*Bemisia argentifolli*), sweetpotato whitefly (*Bemisia tabaci*), citrus whitefly (*Dialeurodes citri*), grapeleaf louse (*Viteus vitifolli*), woolly apple aphid (*Eriosoma langierum*), red scale (*Aonidiella aurantii*), cowpea aphid (*Aphis craccivora*), greenhouse-potato aphid (*Aulacorthum solani*), cabbage aphid (*Brevicoryne brassicae*), potato aphid (*Macrosiphum euphorbiae*), greenhouse whitefly (*Trialeurodes vaporariorum*), green peach aphid (*Myzus persicae*), oat bird-cherry aphid (*Rhopalosiphum padi*), japanese grain aphid (*Sitobion akebiae*), comstock mealybug (*Pseudococcus comstocki*), Inidan wax scale (*Ceroplastes ceriferus*), mulberry scale (*Pseudaulacapsis pentagoa*), cotton aphid (*Aphis gossipii*), and arrowedhead scale (*Unaspis yanonensis*).

Examples of pests belonging to lepidoptera are summer fruit tortrix (*Adoxophyes orana fasciata*), smaller tea tortrix (*Adoxophyes honmai*), apple tortrix (*Archips fuscocupreanus*), oriental fruit moth (*Grapholita molesta*), oriental tea tortrix (*Homona magnanima*), tea leafroller (*Caloptilia theivora*), mugwort looper (*Ascotis selenaria*), grape berry moth (*Endopiza viteana*), codling moth (*Laspeyresia pomonella*), apple leafminer (*Phyllonorycter ringoniella*), apple leaf miner (*Lyonetia prunifoliella malinella*), diamondback moth (*Plutella xylostella*), pink bollworm (*Pectinophora gossypiella*), peach fruit moth (*Carposina niponensis*), peach fruit moth (*Carposina niponensis*), rice stem borer (*Chilo supperssalis*), citrus leafminer (*Phyllocnistis citrella*), yellow rice borer (*Scirpophaga incertulas*), rice leafroller (*Cnaphalocrosis medinalis*), cabbage webworm (*Hellulla undalis*), Chinese yellow swallowtail (*Papilio xuthus*), common white (*Pieris rapae crucivora*), fall webworm (*Hyphantria cunea*), bluegrass webworm (*Parapediasia terrerela*), corn earworm (*Helicoverpa armigera*), cutworm (*Agrotis segetum*), beet semi-looper (*Autographa nigrisigna*), cabbage armyworm (*Mamestra brassicae*), beat armyworm (*Spodoptera exigua*), *Heliothis* (*Heliothis* spp.), and common cutworm (*Spodoptera litura*).

Examples of pests belonging to hymenoptera are cabbage sawfly (*Athalia rosae ruficornis*), rose argid sawfly (*Arge pagana*), and *Formica japonica*. Examples of pests belonging to diptera are rice leafminer (*Agromyza oryzae*), rice leafminer (*Hydrellia griseola*), legume leafminer (*Liriomyza trifolii*), onion maggot (*Delia antiqua*), house fly (*Musca domestica*), Culex pipiens molestus, and house mosquito (*Culex pipiens pallens*).

Examples of pests belonging to thysanoptera are yellow tea thrips (*Scirtothrips dorsalis*), southern yellow thrips (*Thrips palmi*), onion thrips (*Thrips tabaci*), and western flower thrips (*Frankliniella occidentalis*).

Examples of pests belonging to isoptera are Formosan subterranean termites (*Coptotermes formosamus*), japanese subterranean termite (*Reticulitermes speratus*); and examples of pests belonging to Psocoptera are booklice (various spp.), and *Liposcelis bostrychophilus.*

Examples of pests belonging to orthoptera are rice grasshopper (*Oxya yezoensis*), mole crichet (*Gryllotalpa* sp.), American cockroach (*Periplaneta americana*), and German cockroach (*Blatella germanica*).

Examples of pests belonging to acarina are citrus red mite (*Panonychus citri*), two-spotted spider mite (*Tetranychus urticae*), broad mite (*Polyphagotarsonemus latus*), southern false spider mite (*Brevipalpus phoenicis*), clover mite (*Bryobia praetiosa*), pink citrus rust mite (*Aculops pelekassi*), japanese pear rust mite (*Eriophyes chibaensis*), bulb mite (*Rhizoglyphus robini*), fruit tree red spider mite (*Panonychus ulmi*), and mold mite (*Tyrophagus putrescentiae*).

Examples of pests belonging to tylenchida are coffee root-lesion nematode (*Pratylenchus coffeae*), Cobb root-lesion nematode (*Pratylenchus penetrans*), potato cyst nematode (*Globodera rostochiensis*), and southern root-knot nematode (*Meloidogyne incognita*). An example of pests belonging to dolylamida is the needle nematode (*Longidorus* sp.) and an example of pests belonging to gastropoda is the slug (*Incilaria bilineata*).

By effecting the population of insects capable of inflicting damage to the target environment, the formulations may also assist in reducing damage caused by plant viruses, by limiting viral transmission by insect vectors. The most severe damage to target environments occurs through the transmission of plant viruses, primarily begomoviruses, one of the most damaging of which on tomato is the Tomato yellow leaf curl virus (TYLCV).

It has also been found in the course of the investigation leading to the invention of the present application, that the non-volatile vehicle enhances the repelling, insecticidal, pesticidal, ovicidal or antiviral effect exerted by the volatile essential oil, and that the effect exerted by the non-volatile vehicle is enhanced by the volatile essential oil.

Thus, the present invention further provides repellent, insecticidal, pesticidal, ovicidal and antiviral formulations comprising each an effective amount of the formulation of the present invention.

In one embodiment, the formulation may be used as an insect repellent against such insects as the silverleaf whitefly, and as ovicides against such pests as white fly, tomato pinworm and pepper weevil pests.

In one specific embodiment, there is provided a repellent formulation against the whitefly, said formulation comprises encapsulated citronella oil and/or geranium oil and/or tea tree oil and/or lavender oil and/or clove oil and a liquid vehicle comprising pyrethrum and sesame oil.

In another specific embodiment, the formulation against the whitefly comprises encapsulated ginger oil and a liquid vehicle comprising cottonseed oil.

In yet another specific embodiment, there is provided a repellent formulation against the tomato pinworm *Keiferia lycopersicella* (Wals.), said formulation comprises citronella oil and/or geranium oil and/or tea tree oil and/or lavender oil and/or clove oil and a liquid vehicle comprising pyrethrum and sesame oil.

In another embodiment, there is provided an ovicidal or repellent formulation against the pepper weevil, *Anthonomus eugenii Cano*, said formulation comprises citronella oil and/or geranium oil and/or tea tree oil and/or lavender oil and/or clove oil and liquid vehicle comprising pyrethrum and sesame oil.

In another embodiment, the formulation of the present invention may be used against viral transmitting pests capable of acting as viral vectors for infection. The term "viral vector" refers to any such pest as defined and exemplified herein which is capable of carrying and transmitting a plant virus disease-causing, organism.

As stated herein before, the formulation of the present invention makes use of any essential oil contained in microcapsules that may be prepared by any known method. The microcapsules, which are thus prepared, may be either recovered from the reaction mixture and re-suspended in said non-volatile vehicle or in a solution containing thereof. Alternatively, any medium, aqueous or otherwise, which comprises the microcapsules, may be treated without initial separation from the medium in which they are manufactured with at least one non-volatile vehicle. In most cases said medium is water.

In cases where separation is preferred, the recovery of the microcapsules may be achieved, depending on their size, by centrifugation or filtration and washed with several portions of an appropriate solvent, e.g. distilled water, to remove free reactants from the surface. If necessary, the microcapsules may be heated under reduced pressure to further remove any residual reactants from within the microcapsules. Preferably, this procedure is carried out by heating the microcapsule at a temperature above the median glass transition temperature of the polymer making up the microcapsule shell.

These microcapsules may now be dispersed or suspended in said non-volatile liquid or solid vehicle. In some cases, said non-volatile vehicle is a particulate solid, e.g. powder, by which the dispersion is preferably done by admixing an effective amount of dry microcapsules with said vehicle. In some cases, said non-volatile vehicle is a liquid, by which the suspension is preferably prepared by mechanically stirring an effective amount of the microcapsules in said vehicle. The term "effective amount" as used herein refers to an amount determined empirically, which exerts on the target environment the desired effect as is described herein below.

Thus, the present invention further provides a method for the manufacture of the formulation of the present invention, said method comprising dispersing at least one encapsulated essential oil in a non-volatile vehicle or in a medium containing thereof.

The present invention additionally provides a method for the manufacture of the formulation of the present invention, said method comprising adding to any aqueous preparation of encapsulated volatile essential oils an amount of a non-volatile vehicle, as defined hereinabove.

The "aqueous preparation of encapsulated volatile essential oils" is a preparation manufactured by any process known to a person skilled in the art. Preferably said aqueous preparation of encapsulated volatile essential oils is a preparation manufactured in accordance with the process claimed in WO04/98767, said process comprising generally dissolving a di- or polyisocayante into an essential oil, emulsifying the resulting mixture in an aqueous solution containing a di- or polyamine, and/or a di- or polyhydroxy compound to effect encapsulation of said essential oil through interfacial polymerization, whereby there is formed a polyurea and/or polyurethane film around the essential oil droplets, which film enhances the stability of said essential oil, reduces its evaporation rate and controls its release rate when applied to a substrate.

Once manufactured, the liquid or solid formulation (e.g., soluble solids) may be preserved until it is released by some means into the environment. Often it is most convenient to bottle or can the suspension containing the encapsulated essential oil, in which case it may be desirable to add formulation adjuvants to the formulation. “Formulation adjuvants” such as density balancing agents, surfactants, thickeners, biocides, dispersants, antifreeze agents, salts, and the like may be added to improve suspension stability and the ease of application. Such a formulation adjuvant may be added to the suspension of microcapsules at a concentration of from about 0.01% to about 30% by weight of the suspension.

The method for the manufacture of the formulation may include also adding to the liquid vehicle or to the medium, e.g. water, containing it an ionic or non-ionic surfactant. Such surfactant may be added during manufacture of the microcapsules in order to facilitate or control the size of the microcapsules and/or may be added after the microcapsules are manufactured in order to break up a gel that results from the microencapsulation and afford a flowable non-gel formulation. One especially preferred surfactant is sodium dodecyl sulfate (SDS). It may preferably be added in concentrations of 0.1 to 10% and most preferably in concentrations of 0.5% to 5%.

Other non-limiting examples of preferred additives in addition to surfactants are steric barrier polymers, which help maintain particle separation, such as polyvinylpyrrolidone (PVP), polyvinyl alcohol (PVA) and poly(ethoxy)nonylphenol. In some cases it is desirable to adjust the pH of the finished microcapsule formulation as, for example, when the solution of finished microcapsule is combined with other pesticides. Conventional reagents for adjustment of acidity or alkalinity, may be used, including for example, hydrochloric acid, sodium hydroxide, sodium carbonate, and sodium bicarbonate.

In another aspect of the present invention, there is provided a method for managing pest population, said method comprising applying to the target environment or to said pest population or to the loci thereof, the formulation of the present invention.

By “managing pest population” it is meant one or more of the following: driving off a part of or a whole pest population from a selected target environment; controlling future generations; extermination of a part of or a whole pest population; eliminating breeding places; exposing target environment before infestation to the repellent or insecticide formulation; limiting adult, larvae or pest eggs prior to infestation or after infestation has caused damage; and reducing signs of damage. The term “pest population” refers to an adult pest population, larval or nymphal population, egg population, mixed populations, or any combinations thereof, wherein the number of pests in the population may vary from one to several millions.

The term “target environment” as used herein refers to both primary environments, which are susceptible to injury by pest population, and to secondary environments, which surround the primary environments and which do not include any agriculturally or horticulturally desirable target. Primary environments are, for example, leaves, bark, fruit, flowers, seeds, or roots of cereals such as rice, barley, wheat, rye, oat, corn, etc.; beans and peas such as soybean, red bean, broad bean, pea, kidney-bean, peanut, etc.; fruit trees such as apple, citrus, pear, grape, peach, plum, cherry, walnut, chestnut, almond, banana, strawberry, etc.; leafy and fruiting vegetables such as cabbage, tomato, spinach, broccoli, lettuce, onion, stoneleek, Spanish paprika, eggplant, pepper, etc.; root crops such as carrot, potato, sweet potato, taro, radish, lotus rhizome, turnip, burdock, garlic, etc.; processing crops such as cotton, flax, beet, hop, sugarcane, sugar beet, olive, gum, coffee, tobacco, tea, etc.; cucurbitaceous plants such as pumpkin, cucumber, muskmelon, watermelon, melon, etc.; pasture plants such as orchard grass, sorghum, timothy, clover, alfalfa, etc.; lawn grasses; perfumery crops; flowers and ornamental plants; garden-trees such as ginkgo tree, cherry tree, gold-leaf plant, etc.; and timber woods such as white fir, silver fir, pine, hatchet-leaved arbor-vitae, Japan cedar, Japanese cypress, etc.

The target environment may also be a certain pest population against which the formulation may be employed.

In order to control various pests, the formulation of the present invention may be applied to the plants on which appearance of the pest is expected, either as it is or in the form of a dilution or suspension in a proper quantity of water or the like at a concentration effective for the control of the pest population. For instance, for controlling the appearance of pests on edible agriculture products such as fruit trees, cereals and vegetables, the formulation may be used on the surroundings and not directly on the target environment. The formulation may also be adaptable for foliage treatment, seed treatment such as immersion of seeds in the formulation for seed coating, incorporation into the soil, drenching-in-hole treatment, nursery box application, etc.

The formulation of the present invention may be presented, stored, packed or applied as a single formulation, wherein the encapsulated volatile essential oil is pre-mixed with the non-volatile vehicle, or as a two-component formulation, which comprises the encapsulated volatile essential oil as one component, for example in a separate container or applied separately, and the non-volatile vehicle as a second component.

Thus, there is provided a method for managing pest population, said method comprising:

applying to the target environment a microcapsule formulation comprising at least one volatile essential oil, and applying to the target environment a second formulation comprising a non-volatile agent.

The application of the second formulation may be done immediately after the application of the first formulation, or at any time thereafter. A person skilled in the art would be able to decide which of the two methods of managing pest populations disclosed herein is more suitable for the specific case.

The formulation of the present invention may be delivered into the target environment by any method known to a person skilled in the art. Such methods may include for example: (a) manual or mechanical application of the formulation to the soil by, for example, applying a liquid preparation either diluted or undiluted with water to the plant base; (b) applying a granular agent such as dust or a wettable powder to the plant base, planting hole or planting row; (c) ground or aerial spraying of a liquid formulation to the whole field or to specifically selected areas; (d) buying the formulation in the topsoil, etc. The formulation may be applied on pre- or post-harvested fruits and vegetables and may additionally be applied on stored grain pests, house pests, sanitary insect pests and forest pests. Further, the application may also be to construction material of house, using fumigation, bait, etc.

The mode of release of the essential oil from the microcapsule and the ensued effect on the treated environment depends on the physical characteristics of the microcapsule. In accordance with the present invention, the active volatile essential oil is a liquid depot encapsulated by the microcapsule membrane and carried in a non-volatile vehicle, which enhances, either additively or synergistically, its exerted effect. Upon delivery of the formulation to the target environment, the release of the microcapsule's content when applied to the substrate is believed to commence due to the concentration gradient of the volatile essential oils inside and outside of the microcapsule. This release process and its kinetics may be influenced by: (a) drying of the microcapsules; (b) contact with an aqueous media, e.g. water or rain, which causes slow decomposition of the microcapsule shell; (c) high temperatures; and (d) direct sun light. It may, however, be the case that none of these conditions are required or have any effect on any initiation, as the release of the microcapsule content may be spontaneous and independent.

The formulation may also be used for managing pest populations in small gardens, house nurseries, vegetable and flowerbeds, and on few specific specimens such as houseplants.

There is, thus, provided a kit or a commercial package comprising the formulation of the present invention.

The present invention also provides a two-component kit comprising a first container contained therein a suspension of at least one encapsulated volatile essential oil and a second container contained therein a non-volatile vehicle. Optionally, the kits of the present invention may also comprise instructions how to apply the two components to the target environment as to achieve the desirable effect.

The kit formulation or single component formulations may be presented in a solid or a liquid form and in concentrated or diluted state and may be applied to the target environment by, for example, a sponge or a piece of cloth, which was pre absorbed by the formulation, or by hand-held spray.

The invention will now be described by way of examples with reference to the accompanying Figures. While the forgoing description describes in detail only a few specific embodiments of the invention, it will be understood by those skilled in the art that the invention is not limited thereto and that other formulations comprising encapsulated essential oils and non-volatile vehicles may be applied to other types of pests and for other purposes, without departing from the scope of the invention as defined by the appended claims.

DETAILED DESCRIPTION OF THE INVENTION

Example 1

Repellent Formulations Against the White Fly, Tomato Pinworm and Pepper Weevil Formulation 1: Formation of essential oil microcapsules is typically carried out by interfacial polymerization. For example in one case, 17.5 g TDI (toluene diisocyanate) is mixed into 125 g citronella oil, which is added into 250 g water containing 2.5 g PVA using a high sheer mixer. To this is added 70 ml of water with 27.8 g PEG 4000. The mixing is continued for two hours at room temperature. To this dispersant are added 0.4 g of a xanthane gum (rodopol) and 2 g of a fungicide (nefocide). To break up the hydrogel character of this emulsion, 5 g SDS (sodium dodecyl sulfate, 1%) is added.

To this suspension of microcapsules in water are now added 10 g of Pyrethrum oil (50% concentrate) and 1 g sesame oil for every 89 g of suspension.

This general procedure was used to prepare a large number of other repellent formulations, hereon referred to as Formulations 2 to 15.

Formulation 2: This formulation was prepared similarly to Formulation 1 using 93 g citronella oil, 10 g Pyrenthrum and 1 g sesame oil.

Formulation 3: This formulation was prepared similarly to Formulation 1 using geranium oil as the encapsulated volatile essential oil.

Formulation 4: This formulation was prepared similarly to Formulation 1 using tea tree oil as the encapsulated volatile essential oil.

Formulation 5: This formulation was also prepared similarly to Formulation 1 using lavender oil or clove oil as the encapsulated volatile essential oils.

Formulation 6: This formulation was prepared similarly to Formulation 1 using 24.3 ml cottonseed oil and 0.62 ml encapsulated ginger oil.

Formulation 7: This formulation was prepared similarly to Formulation 1 using 23.7 ml cottonseed oil and 1.25 ml encapsulated ginger oil.

Formulation 8: This formulation was prepared similarly to Formulation 1 using 22.5 ml cottonseed oil and 2.5 ml encapsulated ginger oil.

Formulation 9: This formulation was prepared similarly to Formulation 1 using 21.2 ml cottonseed oil and 3.7 ml encapsulated ginger oil.

Formulation 10: This formulation was prepared using the following ingredients and quantities in a process essentially identical to that disclosed for Formulation 1 above: 25 g PVA, 250 g ginger oil, 35 g TDI, 55.6 g PEG 4000, 4 g Nefocide, 10 g SDS and 0.8 g Rodopol.

Formulation 11: This formulation was prepared using the following ingredients and quantities in a process essentially identical to that disclosed for Formulation 1 above: 2.1 g PVA, 110 g ginger oil, 10.1 g TDI, 12.5 g PEG 2000, 1.8 g Nefocide and 0.8 g Rodopol.

Formulation 12: This formulation was prepared using the following ingredients and quantities in a process essentially identical to that disclosed for Formulation 1 above: 2.0 g PVA, 90 g ginger oil, 3.5 g TDI, 0.8 g EDA, 0.7 g EDTA, 1.3 g Nefocide and 1.2 g Rodopol.

Formulation 13: This formulation was prepared using the following ingredients and quantities in a process essentially identical to that disclosed for Formulation 1 above: 2.1 g PVA, 88 g ginger oil, 22 g paraffinic oil. 10.1 g TDI 24.4 g PEG 4000 1.8 g Nefocide and 0.5 g Rodopol.

Formulation 14: This formulation was prepared using the following ingredients and quantities in a process essentially identical to that disclosed for Formulation 1 above: 2.1 g PVA, 88 g ginger oil, 22 g cottonseed oil, 15.3 g TDI, 24.4 g PEG 4000, 1.8 g Nefocide and 0.5 g Rodopol.

Formulation 15: This formulation was prepared using the following ingredients and quantities in a process essentially identical to that disclosed for Formulation 1 above: 2.1 g PVA, 88 g ginger oil, 22 g sesame oil, 22 g TDI, 24.4 g PEG 4000, 1.8 g Nefocide and 0.5 g Rodopol.

Example 2

Application of Repellent Formulations onto a Target Environment

The above formulations were tested on adult silverleaf whiteflies and eggs thereof. The following solutions were used as controls:

1. water

2. Ultra-Fine Oil—a commercial product containing paraffinic oil, and

3. Pyrethrum.

Various leaves of tomato seedlings were treated, top or bottom, with one of the formulations prepared above, and the efficacy of the formulation as a repellent was measured based on the number of whitefly adults repelled therefrom, and based on the number of eggs laid on said treated leaf. Generally speaking, and as may be noted from the below Tables, the efficacy of the formulations were much higher in comparison to the 3 controls used. Furthermore, long-term tests showed that the controls had no substantial effect.

Table 1 shows that Formulation 1 was effective in repelling the whitefly, both in terms of the number of flies which landed on the treated leaf and in terms of the number of eggs laid. For example, as may be noted from Replica 1 of Table 1, the number of flies reduced overall (leaf top+bottom) by 87% from 29 to 4 as compared to a reduction of 50% when treated with Ultra-Fine alone.

Similar results were observed also for Formulations 3 and 4, as shown in Table 2 (some of which are not shown therein)

TABLE 1

Effect of Formulation 1 on the Silverleaf Whitefly.

| Formulation | Untreated Leaf | | Treated Leaf | | Untreated Leaf | Treated Leaf | Untreated adult | Treated adult |
|---|---|---|---|---|---|---|---|---|
| REPLICA 1 | Top | Bottom | Top | Bottom | (# of eggs laid) | (# of eggs laid) | (leaf area) | (leaf area) |
| Ultra-Fine | 0 | | 0 | 8 | 672 | 323 | 260 | 240 |
| Pyrethrum | 0 | 14 | 0 | 10 | 381 | 341 | 213 | 199 |
| Water | 0 | 18 | 0 | 28 | 579 | 803 | 232 | 201 |
| Form. 1 | 0 | 29 | 0 | 4 | 696 | 89 | 230 | 225 |
| | Untreated Leaf | | Treated Leaf | | Untreated Leaf | Treated Leaf | Untreated adult | Treated adult |
| REPLICA 2 | Top | Bottom | Top | Bottom | (# of eggs laid) | (# of eggs laid) | (leaf) | (leaf) |
| Ultra-Fine | 0 | 35 | 1 | 13 | 403 | 93 | 159 | 155 |
| Pyrethrum | 0 | 27 | 0 | 14 | 184 | 101 | 203 | 192 |
| Water | 0 | 30 | 0 | 17 | 302 | 183 | 170 | 158 |
| Form. 1 | 0 | 39 | 0 | 3 | 224 | 14 | 219 | 201 |
| | Untreated Leaf | | Treated Leaf | | Untreated Leaf | Treated Leaf | Untreated adult | Treated adult |
| REPLICA 3 | Top | Bottom | Top | Bottom | (# of eggs laid) | (# of eggs laid) | (leaf) | (leaf) |
| Ultra-Fine | 0 | 12 | 0 | 4 | 572 | 233 | 187 | 131 |
| Pyrethrum | 0 | 8 | 0 | 0 | 565 | 1 | 170 | 135 |
| Water | 0 | 6 | 0 | 8 | 466 | 297 | 183 | 143 |
| Form. 1 | 0 | 7 | 0 | 1 | 343 | 4 | 143 | 118 |

TABLE 2

Effect of Formulations 3 and 4 on the White fly.

| | UNTREATED | | | | TREATED | | | |
|---|---|---|---|---|---|---|---|---|
| | ADULTS | | | Leaf Area | ADULTS | | | |
| | Top | Bottom | EGGS | ($cm^2$) | Top | Bottom | EGGS | Leaf Area |
| Formulation REPLICA 1 Formulation No. | | | | | | | | |
| Ultra-Fine | 0 | 4 | 243 | 85.18 | 0 | 3 | 167 | 126.33 |
| Pyrethrum | 0 | 3 | 47 | 57.59 | 0 | 3 | 139 | 88.61 |
| Water | 0 | 2 | 114 | 68.76 | 0 | 8 | 172 | 77.44 |
| Formulation 3 | 0 | 3 | 95 | 100.83 | 0 | 0 | 29 | 119.64 |
| REPLICA 2 | | | | | | | | |
| Ultra-Fine | 0 | 4 | 117 | 69.07 | 0 | 3 | 108 | 32.95 |
| Pyrethrum | 0 | 7 | 224 | 50.33 | 0 | 7 | 202 | 51.06 |
| Water | 0 | 5 | 238 | 62.27 | 0 | 11 | 384 | 66.37 |
| Formulation 3 | 0 | 11 | 335 | 81.22 | 0 | 0 | 58 | 60.03 |
| REPLICA 3 | | | | | | | | |
| Ultra-Fine | 0 | 8 | 312 | 105.53 | 0 | 2 | 48 | 80.89 |
| Pyrethrum | 0 | 4 | 110 | 105.2 | 0 | 0 | 0 | 58.96 |
| Water | 0 | 11 | 227 | 101.41 | 0 | 9 | 247 | 56.86 |
| Formulation 3 | 0 | 11 | 242 | 59.35 | 0 | 4 | 117 | 77.37 |
| Ultra-Fine | 0 | 0 | 12 | 18.92 | 0 | 1 | 0 | 23.48 |

TABLE 2-continued

Effect of Formulations 3 and 4 on the White fly.

| | UNTREATED | | | | TREATED | | | |
|---|---|---|---|---|---|---|---|---|
| | ADULTS | | | Leaf Area | ADULTS | | | |
| | Top | Bottom | EGGS | (cm$^2$) | Top | Bottom | EGGS | Leaf Area |
| Pyrethrum | 0 | 3 | 3 | 20.3 | 0 | 1 | 0 | 20.23 |
| Water | 0 | 1 | 19 | 26.25 | 0 | 6 | 76 | 32.28 |
| Formulation 4 | 0 | 2 | 38 | 16.83 | 0 | 2 | 16 | 15.03 |

TABLE 3

The Affect of Encapsulated Formulations on white fly Populations on Tomato Plants

| | Treated Plants | | | Non treated Plants | | |
|---|---|---|---|---|---|---|
| | Number of whiteflies | | | Number of whiteflies | | |
| Formulation | Leaf Top | Leaf Bottom | No. eggs | Leaf Top | Leaf Bottom | No. eggs |
| A | 0 | 3 | 25 | 0 | 15 | 61 |
| B | 0 | 0 | 0 | 0 | 18 | 150 |
| C | 0 | 0 | 12 | 0 | 23 | 93 |
| D | 0 | 5 | 0 | 0 | 18 | 35 |
| E | 0 | 2 | 10 | 0 | 15 | 64 |
| F | 0 | 10 | 44 | 0 | 11 | 21 |
| G | 0 | 12 | 20 | 0 | 10 | 39 |

For the next set of experiments, the following seven formulations were prepared and used:

A. 95 ml cottonseed oil and 5 ml Tween

B. 24.4 ml cottonseed oil and 0.63 ml encapsulated ginger oil

C. 23.7 ml cottonseed oil and 1.2 ml encapsulated ginger oil

D. 22.5 ml cottonseed oil and 2.5 ml encapsulated ginger oil

E. 21.2 ml cottonseed oil and 3.75 ml encapsulated ginger oil

F. Ultra-Fine Oil

G. Water.

The results of the experiments conducted respectful of repelling the whitefly population from tomato plants are shown in Table 3. As may be noted, the formulations which were prepared in accordance with the present invention were much more effective in repelling whiteflies and in reducing the number of eggs laid.

The invention claimed is:

1. An essential oil formulation comprising at least one volatile essential oil having a pest repelling, insecticidal, pesticidal, larvicidal and/or ovicidal effect, and a non-volatile vehicle in a solid or a liquid form, said non-volatile vehicle comprising a non-volatile oil, said at least one volatile essential oil being encapsulated and separate from said non-volatile oil, wherein said non-volatile vehicle enhances the pest repelling, insecticidal, pesticidal and/or ovicidal effect of the volatile essential oil and wherein said non-volatile is selected from sesame oil, pyrethrum oil, and combinations thereof, and wherein said at least one volatile essential oil is selected from cinnamon, cedar, castor, clove, geranium, lemongrass, mint, thyme, turmeric, wintergreen, rosemary, anise, cardamom, chamomile, coriander, cumin, dill, mint, parsley, lavender, basil, camphor, citronella, eucalyptus, fennel, ginger, grapefruit, lemon, mandarin, orange, pine needle, pepper, rose, sweet orange, tangerine, tea tree, tea seed, caraway, garlic, peppermint, onion, and spearmint.

2. The formulation of claim 1 further comprising at least one additive selected from the group of adjuvants, adhesives, antioxidants, water-resistant agents, surfactants, steric barrier polymers which prevent microcapsule aggregation and gel-breaking agents, as part of the vehicle or within the microcapsule.

3. The formulation of claim 1 further comprising at least one agent selected from pesticides, insect growth regulators, herbicides, insecticides, acaracides, fungicides, nematicides, ectoparasiticides, and combinations thereof, wherein said at least one agent is encapsulated with said at least one volatile essential oil.

4. The formulation of claim 3, wherein said agent is a pesticide selected from the group of carbamates, ureas, triazines, triazoles, uracils, organophosphates, morpholines, dinitroanilines, acylalanines, pyrethroids, organochlorines, carbofuran, azinphos-methyl, sulfentrazone, carfentrazone-ethyl, cypermethrin, cyromazine, beta-cyfluthrin, endosulfan, phosmet, chlorobromuron, chloroxuron, chlorotoluron, fluometuron, metobromuron, thiazafluron, teflubenzuron, hexaflumuron, diflubenzuron, flufenoxuron, lufenuron, chlorfluazuron, riovaluron, dimethachlor, metolachlor, pretilachlor, 2-chloro-n-(l-methyl-2-methoxyethyl)-acet-2,6-xylidide, imidocloprid, alachlor, butachlor, propachlor, dimethenamid, bifenox, 4-(4-pentyn-l-yloxy)diphenylether, acifluorfen, oxyfluorfen, fluoroglycofen-ethyl, fomesafen, cis, trans-(+)-2-ethyl-5-(4-phenoxyphenoxymethyl)-1,3-dioxolane, fluazifopbutyl, haloxyfop-methyl, haloxyfop-(2-ethoxyethyl), endosulfan, fluorotopic, fenoxapropethyl, quizalofop-ethyl, propaquizafop, diclofop-methyl, butralin, ethalfluralin, fluchloral1in, isopropalin, pendimethalin, profluralin, trifluralin, aclalanines furalaxyl, metalaxyl, benzoylprop ethyl, flamprop methyl, difenoconazole, etaconazol, propiconazole, 1,2-(2,4-dichlorophenyl)-pent-l-yl-1h-1,2,4- triazole, triadimefon, dioxacarb, furathiocarb, aldicarb, benomyl, 2-sec-, butylphenylmethylcarbamate, etiofencarb, fenoxycarb, isoprocarb, propoxur, carbetamid, butylate, diallat, eptc, molinate, thiobencarb, tri-allate, vemolate, piperophos, anilofos, butamifos, azamethiphos, chlorfenvinphos, dichlorvos, diazinon, methidathion, azinphos ethyl, azinphos methyl, chlorpyrifos, chlorthiofos, crotoxyphos, cyanophos, demeton, dialifos, dimethoate, disulfoton, etrimfos, famphur, flusulfothion, fluthion, fonofos, formothion, heptenophos, isofen:phos, isoxathion, malathion, mephospholan, mevinphos, naled, oxydemeton methyl, oxydeprofos, parathion, phoxim, pyrimiphos methyl, profenofos, propaphos, propetamphos, prothiophos, quinalphos, sulprofos, phemephos, terbufos, triazophos, trichloronate, fenamipos, isazophos, s-benzylo, o-diisopropylphosphorothioate, edinphos and pyrazophos.

5. The formulation of claim 1 in a preparation form selected from emulsifiable concentrate, wettable powder, granular wettable powder, flowable preparation, suspension, granule, dust, fumigant, solution, and aqueous solution.

6. The formulation of claim 1, wherein the formulation is for management of pest populations.

7. The formulation of claim 1 wherein the formulation controls populations of whiteflies, tomato pinworms, armyworms, stinkbugs pepper weevil pests or combinations thereof.

8. The formulation of claim 1, wherein the non-volatile vehicle is not encapsulated together with said at least one volatile essential oil.

9. The formulation of claim 1, wherein the at least one volatile essential oil is encapsulated by a microcapsule membrane.

10. The formulation of claim 9, wherein the at least one volatile essential oil is released from the microcapsule membrane due to a concentration gradient of the at least one volatile essential oil inside and outside of the microcapsule.

11. The formulation of claim 1, wherein the at least one volatile essential oil is pre-mixed with the non-volatile vehicle.

12. The formulation of claim 1, wherein the formulation is a two-component formulation, wherein the at least one volatile essential oil is a first component and the non-volatile vehicle is a second component that is applied separately from the first component.

13. The formulation of claim 1, wherein said at least one volatile essential oil being encapsulated within a mixture or a suspension.

14. The formulation of claim 1, wherein said non-volatile oil is a mixture of sesame oil and pyrethrum oil.

15. A commercial package comprising the formulation according to claim 1.

16. An essential oil formulation comprising at least one volatile essential oil having a pest repelling, insecticidal, pesticidal, larvicidal and/or ovicidal effect, and a non-volatile vehicle in a solid or a liquid form, said non-volatile vehicle comprising a non-volatile oil, said at least one volatile essential oil being encapsulated and separate from said non-volatile oil, wherein said non-volatile vehicle enhances the pest repelling, insecticidal, pesticidal and/or ovicidal effect of the volatile essential oil and wherein said non-volatile oil is selected from sesame oil, a mixture of sesame oil and pyrethrum oil, a mixture of cottonseed oil and pyrethrum oil and combinations thereof, and wherein said at least one volatile essential oil is selected from cinnamon, cedar, castor, clove, geranium, lemongrass, mint, thyme, turmeric, wintergreen, rosemary, anise, cardamom, chamomile, coriander, cumin, dill, mint, parsley, lavender, basil, camphor, citronella, eucalyptus, fennel, ginger, grapefruit, lemon, mandarin, orange, pine needle, pepper, rose, sweet orange, tangerine, tea tree, tea seed, caraway, garlic, peppermint, onion, and spearmint.

17. A method for the manufacture of the formulation of claim 1 comprising dispersing the at least one encapsulated volatile essential oil in the non-volatile vehicle or in a medium containing the non-volatile vehicle.

18. A method for the manufacture of the formulation of claim 1 comprising adding to any aqueous preparation of the encapsulated volatile essential oil an amount of the non-volatile vehicle.

19. The method according to claim 18, wherein said encapsulated volatile essential oils are manufactured through interfacial polymerization.

20. The method according to claim 19, wherein said interfacial polymerization affects encapsulation of said volatile essential oil, whereby there is formed a poly urea and/or polyurethane film around droplets of said volatile essential oil.

21. A method for managing a pest population, said method comprising applying to a target environment or to a pest population or to a loci thereof, a formulation according to claim 1.

22. The method according to claim 21, wherein said target environment is a primary environment or a secondary environment.

23. The method according to claim 22, wherein said primary environment is selected from leaves, bark, fruits, flowers, seeds or roots of cereals, beans peas, fruit trees walnut, chestnut, almond, leafy vegetables, fruiting vegetables, root crops, processing crops, cucurbitaceous plants, pasture plants, lawn grasses, perfumery crops, ornamental plants, and timber woods.

* * * * *